United States Patent
Parthasaradhi Reddy et al.

(10) Patent No.: US 8,552,036 B2
(45) Date of Patent: Oct. 8, 2013

(54) POLYMORPH OF ATAZANAVIR SULFATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Research Foundation (IN)

( * ) Notice: Subject to any disclaimer, the term of this patent is extended or adjusted under 35 U.S.C. 154(b) by 135 days.

(21) Appl. No.: 13/121,443

(22) PCT Filed: Jan. 12, 2009

(86) PCT No.: PCT/IN2009/000034
§ 371 (c)(1),
(2), (4) Date: Mar. 29, 2011

(87) PCT Pub. No.: WO2010/079497
PCT Pub. Date: Jul. 15, 2010

(65) Prior Publication Data
US 2012/0015987 A1    Jan. 19, 2012

(51) Int. Cl.
*A61K 31/4402*    (2006.01)
*C07D 213/56*    (2006.01)

(52) U.S. Cl.
USPC .......................... 514/357; 546/332

(58) Field of Classification Search
USPC .......................... 546/332; 514/357
See application file for complete search history.

(56) References Cited

U.S. PATENT DOCUMENTS

| | | | |
|---|---|---|---|
| 3,663,607 A | 5/1972 | Barrett et al. | |
| 3,836,671 A | 9/1974 | Barrett et al. | |
| 6,087,383 A | 7/2000 | Singh et al. | |
| 6,627,646 B2 * | 9/2003 | Bakale et al. | 514/322 |
| 2005/0256202 A1 | 11/2005 | Kim et al. | |

FOREIGN PATENT DOCUMENTS

| | | |
|---|---|---|
| DE | 2007751 | 9/1970 |
| WO | 9936404 A1 | 7/1999 |
| WO | 2005108349 A2 | 11/2005 |

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1033.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
International Preliminary Report on Patentability; International Application No. PCT/IN2009/000034; International Filing Date Jan. 12, 2009; Date of Mailing Oct. 20, 2011, 5 pages.
International Search Report and Written Opinion; International Application No. PCT/IN2009/000034; International Filing Date Jan. 12, 2009; Date of Mailing Sep. 22, 2011; 7 pages.
"Effects Due to Compression"; in Polymorphism in Pharmaceutical Solids; Marcel Dekker, Inc.; Harry G. Brittain, ed.; p. 348; 3 pages; 2008.

* cited by examiner

*Primary Examiner* — Patricia L Morris
(74) *Attorney, Agent, or Firm* — Cantor Colburn LLP

(57) ABSTRACT

The present invention provides a novel crystalline form of atazanavir sulfate, process for its preparation and to pharmaceutical composition containing it. In accordance with the present invention atazanavir sulfate was dissolved in methanol, to the solution was added ethyl acetate, the solid obtained was collected by filtration and dried to give atazanavir sulfate crystalline form H1.

5 Claims, 2 Drawing Sheets

POLYMORPH OF ATAZANAVIR SULFATE

FIELD OF THE INVENTION

The present invention provides a novel crystalline form of atazanavir sulfate, process for its preparation and to pharmaceutical composition containing it.

BACKGROUND OF THE INVENTION

Atazanavir sulfate is known by the chemical name (3S,8S, 9S,12S)-3,12-bis(1,1-dimethylethyl)-8-hydroxy-4,11-dioxo-9-(phenylmethyl)-6-[[4-(2-pyridinyl) phenyl]methyl]-2, 5,6,10,13-pentaazatetradecanedioic acid dimethyl ester sulfate. Atazanavir sulfate is an antiviral agent and anti-HIV protease inhibitor. Atazanavir sulfate is represented by the following structure:

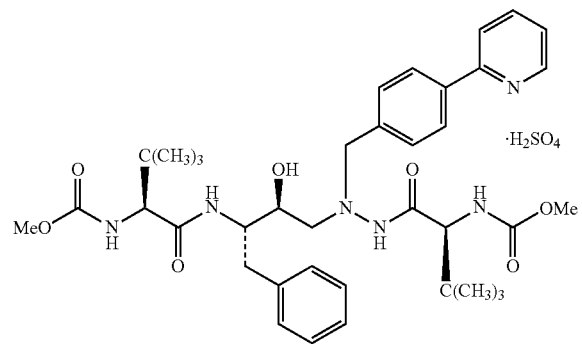

Atazanavir and its sulfate salt may be prepared using the procedures described in DE Patent No. 2007751, U.S. Pat. No. 3,663,607 and U.S. Pat. No. 3,836,671.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining a crystalline form over the other.

Atazanavir sulfate can exist in different polymorphic form, which differ from each other in terms of stability, physical properties, spectral data and methods of preparation.

U.S. Pat. No. 6,087,383 described the preparation of atazanavir bisulfate in the form of Type-I crystals which appear to be an anhydrous/desolvated crystalline form and Type-II crystals which are a hydrated, hygroscopic crystalline form.

WO Patent Publication No. 2005/108349 disclosed two crystal forms, pattern C, form E3 of atazanavir bisulfate and also disclosed process for the preparation of atazanavir bisulfate form A (equivalent to Type 1 crystals obtained in Example 3 of U.S. Pat. No. 6,087,383). According to WO Patent Publication No. 2005/108349, pattern C crystals of atazanavir bisulfate was obtained by stirring a suspension of the form A crystals of atazanavir bisulfate in water.

We have discovered a stable novel crystalline form of atazanavir sulfate. The novel crystalline form is stable over the time and has good flow properties and so, the novel crystalline form is suitable for formulating atazanavir sulfate.

One object of the present invention is to provide a novel crystalline form of atazanavir sulfate and a process for preparing it.

According to another object of the present invention is to provide pharmaceutical compositions containing the novel crystalline form of atazanavir sulfate.

DETAILED DESCRIPTION OF THE INVENTION

According to one aspect of the present invention, there is provided a novel crystalline form of atazanavir sulfate designated as atazanavir sulfate form H1 characterized by peaks in the powder x-ray diffraction spectrum having 2θ angle positions at about 4.1, 13.6, 18.5, 19.5, 20.1 and 24.3±0.2 degrees. The powdered x-ray diffractogram (PXRD) of atazanavir sulfate crystalline form H1 is shown in FIG. 1.

The atazanavir sulfate crystalline form H1 may be identified and differentiated from the known polymorphs by its characteristic PXRD pattern. Thus, for example, a peak at 13.6±0.2 degrees 2θ is present in the PXRD of the atazanavir sulfate crystalline form H1 of the present invention, but is absent in the PXRD of the crystalline form of atazanavir bisulfate pattern C disclosed in the WO Patent Publication No. 2005/108349.

Atazanavir sulfate crystalline form H1 of present invention is further characterized by a Differential Scanning calorimetry (DSC) thermogram as shown in FIG. 2.

According to another aspect of the present invention, there is provided a process for preparation of atazanavir sulfate form H1, which comprises:
 a) dissolving atazanavir sulfate in methanol;
 b) adding an anti solvent or a mixture of anti solvents selected from ethyl acetate, isopropyl acetate and butyl acetate to the solution obtained in step (a); and
 c) isolating atazanavir sulfate crystalline form H1.
Preferable anti solvent is ethyl acetate.

According to another aspect of the present invention, there is provided a pharmaceutical composition comprising atazanavir sulfate crystalline form H1 and a pharmaceutically acceptable excipient.

Preferable pharmaceutical composition of atazanavir sulfate crystalline form H1 is a solid oral dosage form, comprising atazanavir sulfate crystalline form H1.

Figure 1:
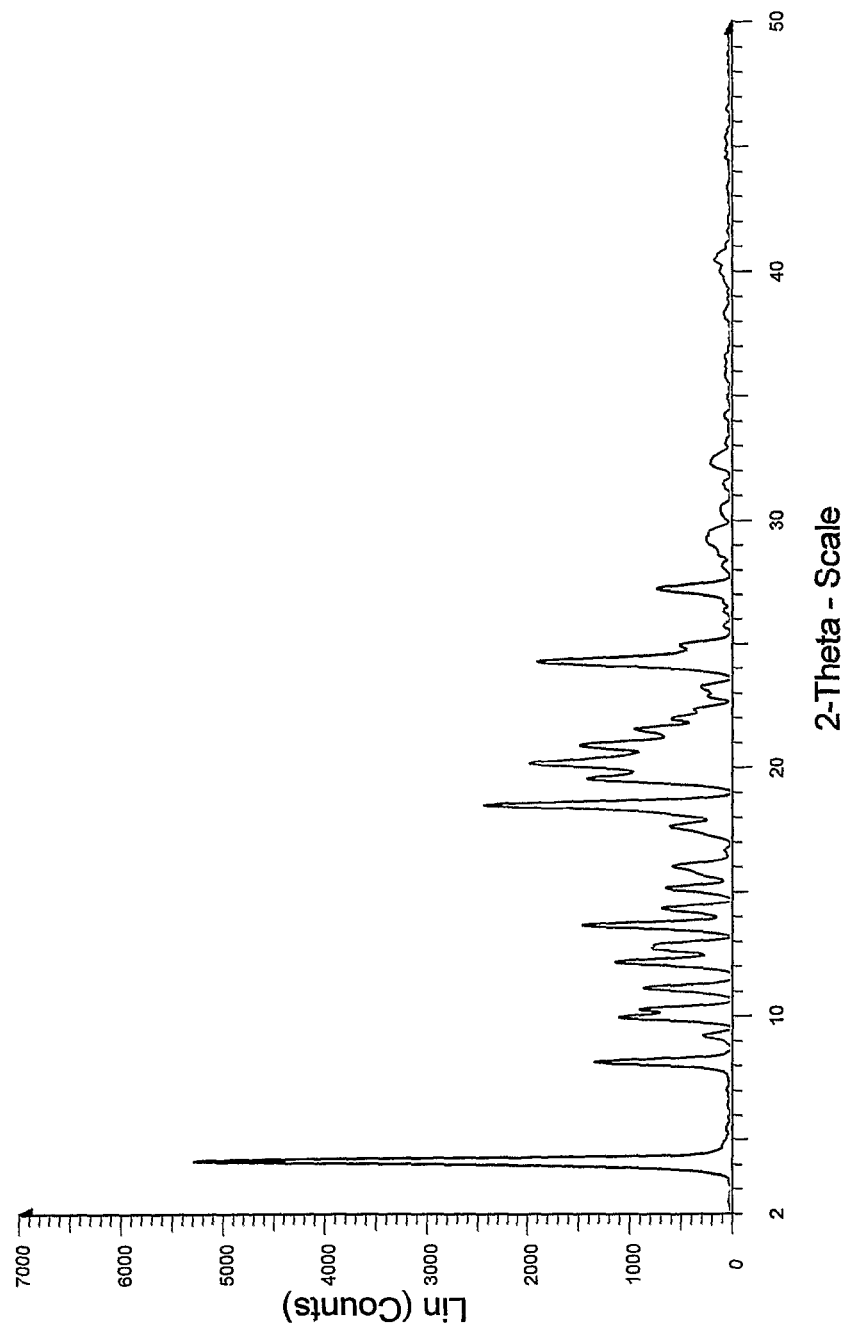
FIG. 1 is X-ray powder diffraction spectrum of atazanavir sulfate crystalline form H1.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.03 degrees to theta per step and a step of 0.5 seconds. The sample was simply placed on the sample holder. The sample was rotated at 30 rpm at a voltage 40 KV and current 35 mA.

DSC (Differential Scanning calorimetry) measurements were performed with a DSC Q10 (TA Instruments, Inc.). About 3 mg of the powder was placed in an open aluminum pan and it was crimped with an aluminum lid. The crimped sample was then placed in the DSC cell opposite to empty aluminum pan (as reference) and the sample was scanned at 10° C./min from 50° C. to 250° C.

The invention will now be further described by the following example, which is illustrative rather than limiting.

EXAMPLE 1

Atazanavir sulfate (10 gm) was dissolved in methanol (50 ml) at room temperature and stirred for 20 minutes at room temperature. To the solution was added ethyl acetate (300 ml) at room temperature and stirred for 30 minutes at room temperature. The solid obtained was collected by filtration and the solid was washed with ethyl acetate (30 ml), and then dried at 50-55 deg C for 3 hours to obtain 7 gm of atazanavir sulfate crystalline form H1.

EXAMPLE 2

Atazanavir sulfate (15 gm) was dissolved in methanol (75 ml) at room temperature. Ethyl acetate (570 ml) was added to the solution at room temperature and stirred for 45 minutes at room temperature. The solid obtained was collected by filtration and the solid was washed with ethyl acetate (50 ml), and then dried at 50-55 deg C for 4 hours to obtain 11 gm of atazanavir sulfate crystalline form H1.

We claim:

1. Atazanavir sulfate crystalline form H1, characterized by an X-ray powder diffractogram having peaks expressed as 2θ angle positions at about 4.1, 13.6, 18.5, 19.5, 20.1 and 24.3± 0.2 degrees.

Figure 2:
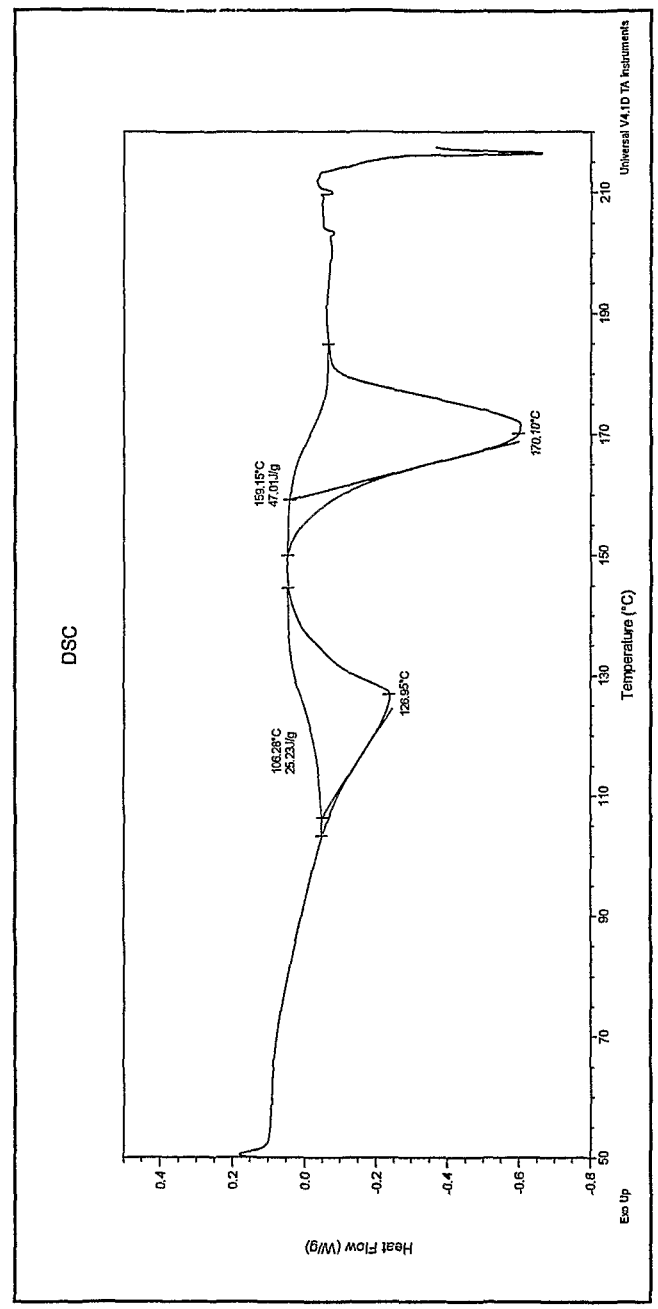
FIG. 2 is Differential scanning calorimetry (DSC) thermogram of atazanavir sulfate crystalline form H1.

2. The atazanavir sulfate crystalline form H1 as claimed in claim 1, wherein the atazanavir sulfate crystalline form H1 is further characterized by a differential scanning calorimetry thermogram as shown in FIG. 2.

3. A process for the preparation of atazanavir sulfate crystalline form H1 as defined in claim 1, which comprises:
   a. dissolving atazanavir sulfate in methanol;
   b. adding an anti solvent or a mixture of anti solvents selected from ethyl acetate, isopropyl acetate and butyl acetate to the solution obtained in step (a); and
   c. isolating atazanavir sulfate crystalline form H1.

4. The process as claimed in claim 3, wherein the anti solvent is ethyl acetate.

5. A pharmaceutical composition comprising atazanavir sulfate crystalline form H1 and a pharmaceutically acceptable excipient in the form of a solid oral dosage form.

* * * * *